(12) United States Patent
An

(10) Patent No.: US 8,210,084 B2
(45) Date of Patent: Jul. 3, 2012

(54) STENT AND METHOD FOR MANUFACTURING THE SAME

(75) Inventor: Sung-Soon An, Seoul (KR)

(73) Assignee: Standard Sci-Tech, Inc., Seoul (KR)

( * ) Notice: Subject to any disclaimer, the term of this patent is extended or adjusted under 35 U.S.C. 154(b) by 0 days.

(21) Appl. No.: 13/012,946

(22) Filed: Jan. 25, 2011

(65) Prior Publication Data

US 2011/0125250 A1  May 26, 2011

Related U.S. Application Data

(62) Division of application No. 11/914,490, filed on Nov. 15, 2007, now abandoned.

(30) Foreign Application Priority Data

Jul. 15, 2005  (KR) .................. 10-2005-0064359
Jul. 7, 2006  (WO) ................ PCT/KR2006/002652

(51) Int. Cl.
*D04C 1/06* (2006.01)

(52) U.S. Cl. .......................................................... 87/13

(58) Field of Classification Search ..... 87/13; 623/1.15, 623/1.2, 1.22
See application file for complete search history.

(56) References Cited

U.S. PATENT DOCUMENTS

| | | | |
|---|---|---|---|
| 5,061,275 A | 10/1991 | Wallsten et al. | |
| 5,545,211 A | 8/1996 | An et al. | |
| 5,643,339 A | 7/1997 | Kavteladze et al. | |
| 5,746,765 A | 5/1998 | Kleshinski et al. | |
| 5,800,519 A | 9/1998 | Sandock | |
| 5,876,432 A * | 3/1999 | Lau et al. ..................... | 623/1.13 |
| 6,007,574 A * | 12/1999 | Pulnev et al. ................ | 623/1.15 |
| 6,063,113 A | 5/2000 | Kavteladze et al. | |
| 6,221,100 B1 | 4/2001 | Strecker | |
| 6,241,757 B1 | 6/2001 | An et al. | |
| 6,730,117 B1 | 5/2004 | Tseng et al. | |
| 6,792,979 B2 | 9/2004 | Konya et al. | |
| 2002/0033552 A1 | 3/2002 | Matsutani et al. | |
| 2002/0040236 A1* | 4/2002 | Lau et al. ..................... | 623/1.12 |
| 2002/0183828 A1* | 12/2002 | Park et al. ................... | 623/1.15 |
| 2003/0040771 A1 | 2/2003 | Hyodoh et al. | |
| 2003/0074051 A1* | 4/2003 | Freislinger Luehrs ....... | 623/1.15 |
| 2004/0143318 A1 | 7/2004 | Tseng et al. | |
| 2004/0186549 A1 | 9/2004 | Jayaraman | |
| 2005/0137702 A1* | 6/2005 | Haug et al. .................. | 623/2.38 |
| 2005/0283962 A1 | 12/2005 | Boudjemline | |
| 2006/0136043 A1 | 6/2006 | Cully et al. | |
| 2007/0203570 A1 | 8/2007 | Becker | |
| 2007/0219618 A1 | 9/2007 | Cully et al. | |

FOREIGN PATENT DOCUMENTS

CN  1402624 A  3/2003

(Continued)

*Primary Examiner* — Shaun R Hurley

(74) *Attorney, Agent, or Firm* — Summa, Additon & Ashe, P.A.

(57) ABSTRACT

A method of manufacturing a stent includes forming a first cylindrical mesh structure by bending a first member in a zigzag-shape having peaks and valleys and a plurality of turns wound around an outer circumference of a manufacturing frame and forming a second cylindrical mesh structure by bending a second member in a zigzag-shape having peaks and valleys and a plurality of turns wound around an outer circumference of a manufacturing frame, wherein a bending track the second member crosses a bending track of the first member.

6 Claims, 6 Drawing Sheets

FOREIGN PATENT DOCUMENTS

| | | |
|---|---|---|
| JP | 8-509899 | 10/1996 |
| JP | 09-094626 | 4/1997 |
| JP | 10-272190 | 10/1998 |
| JP | 11-042284 | 2/1999 |
| JP | 2006-506201 A | 2/2006 |
| WO | 95/26695 | 10/1995 |
| WO | 01-41673 A1 | 6/2001 |
| WO | 2004105853 A1 | 12/2004 |
| WO | 2007011122 A1 | 1/2007 |

* cited by examiner

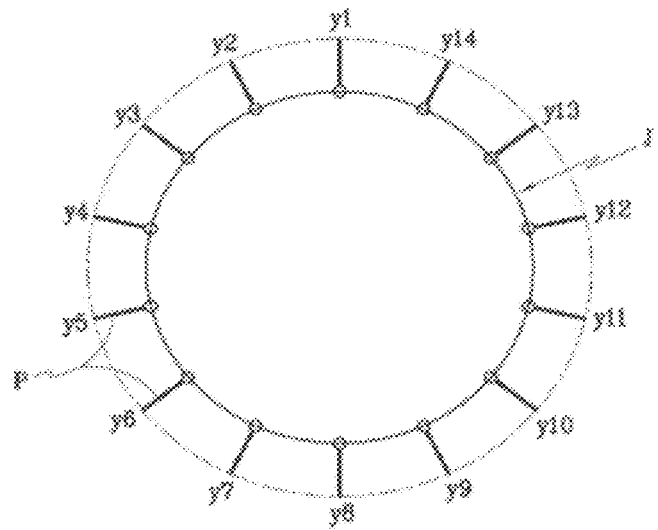
[Fig. 1]
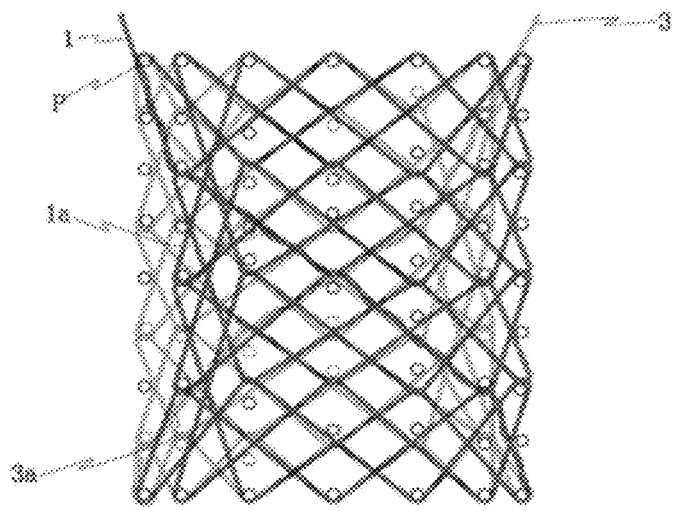
[Fig. 2]
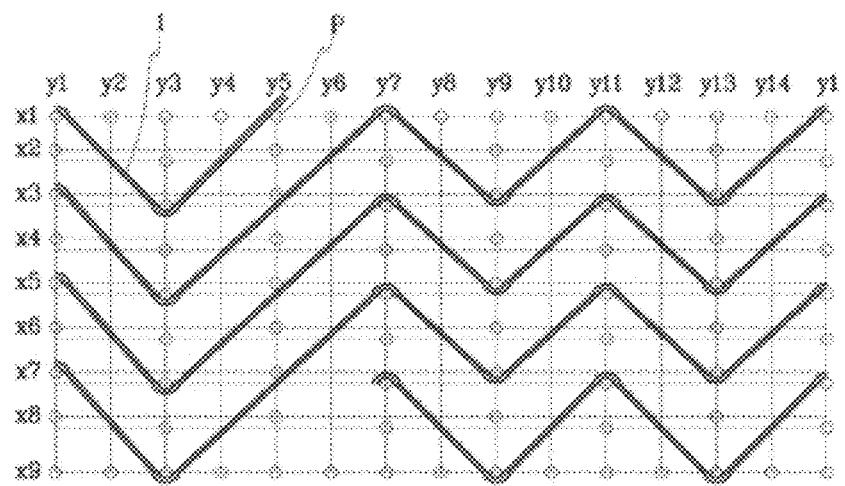

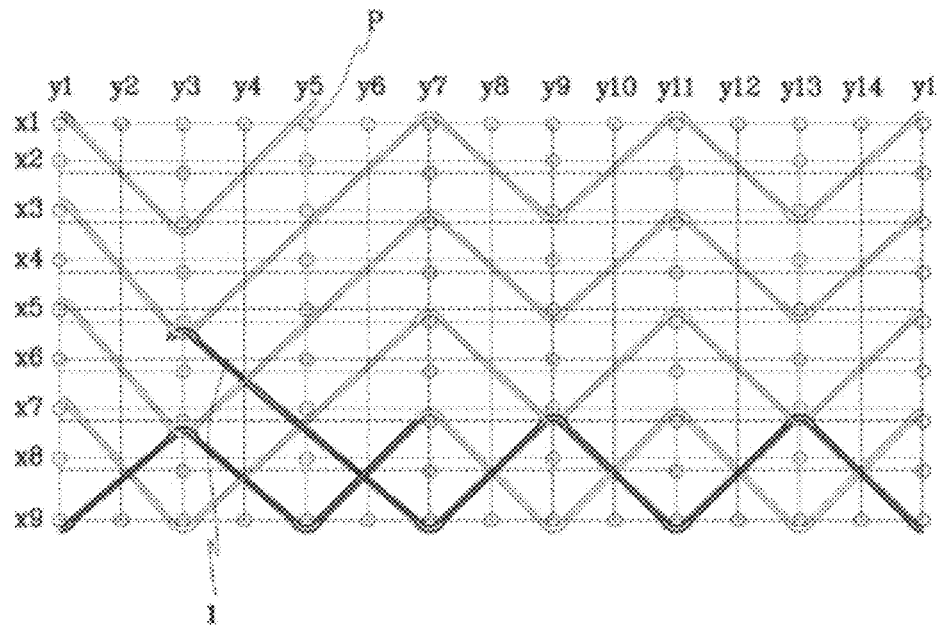
[Fig. 3]
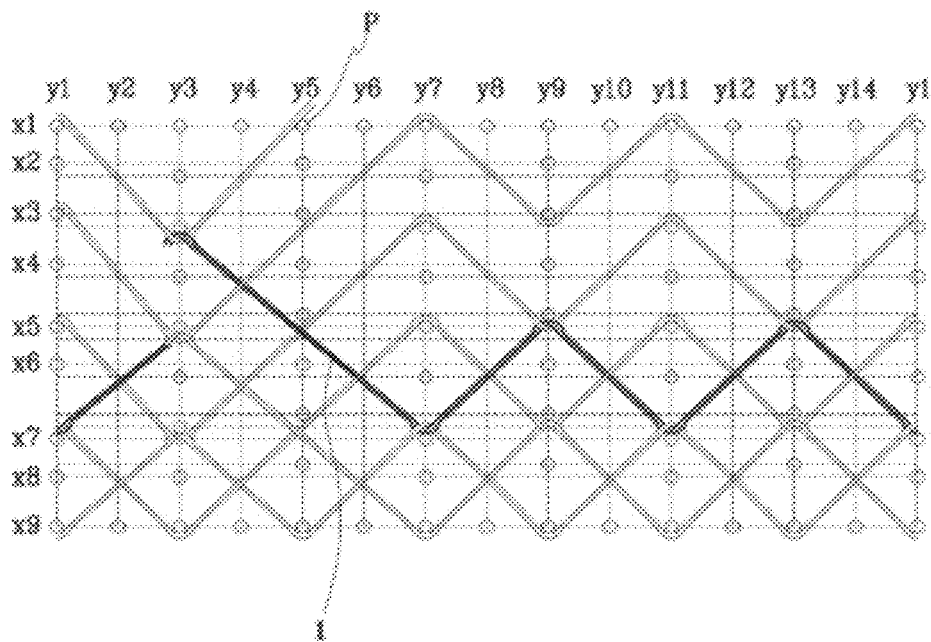
[Fig. 4]

[Fig. 5]
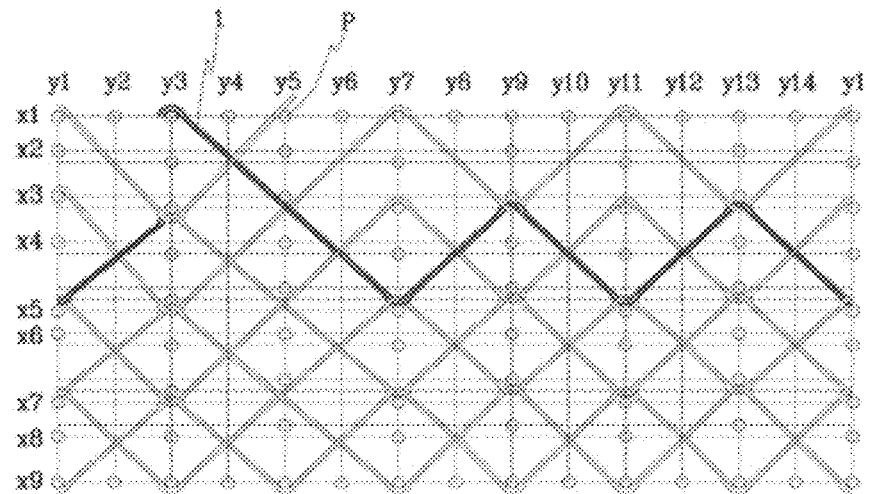
[Fig. 6]
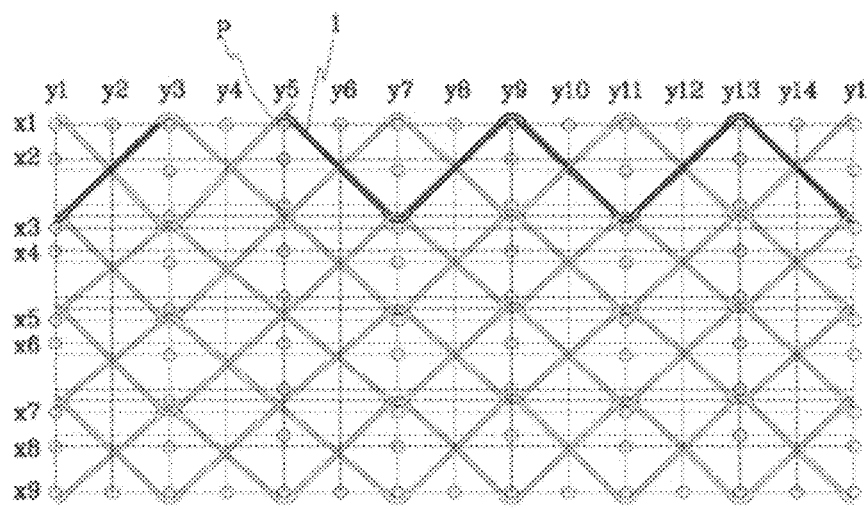
[Fig. 7]
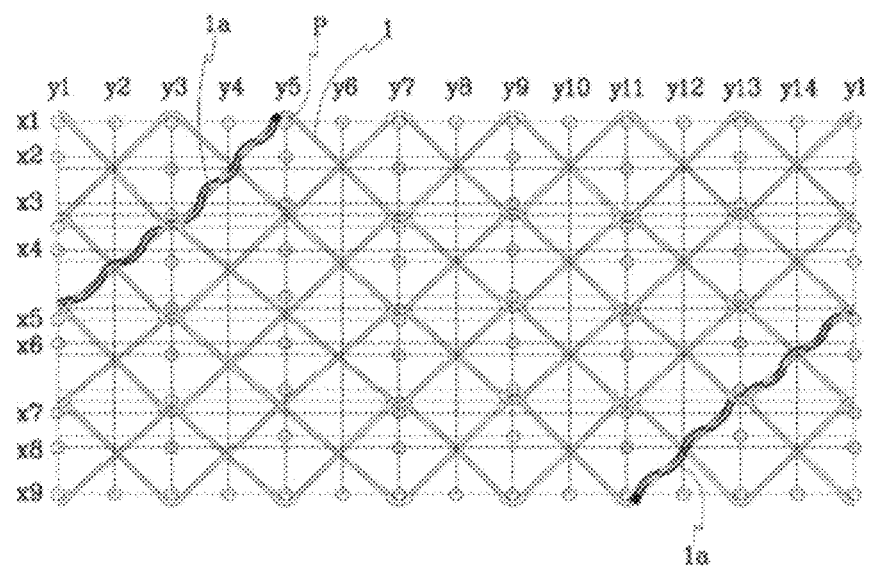

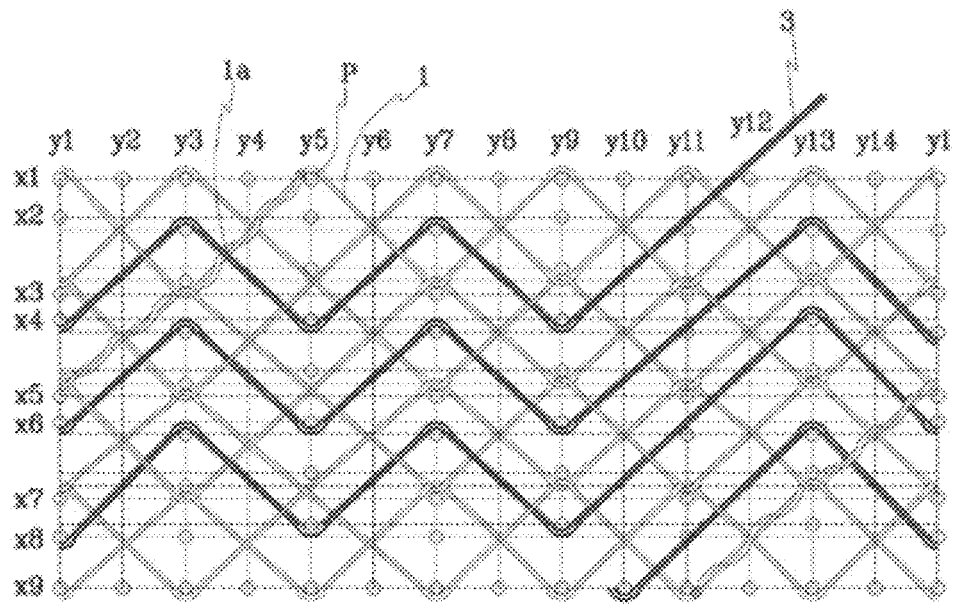
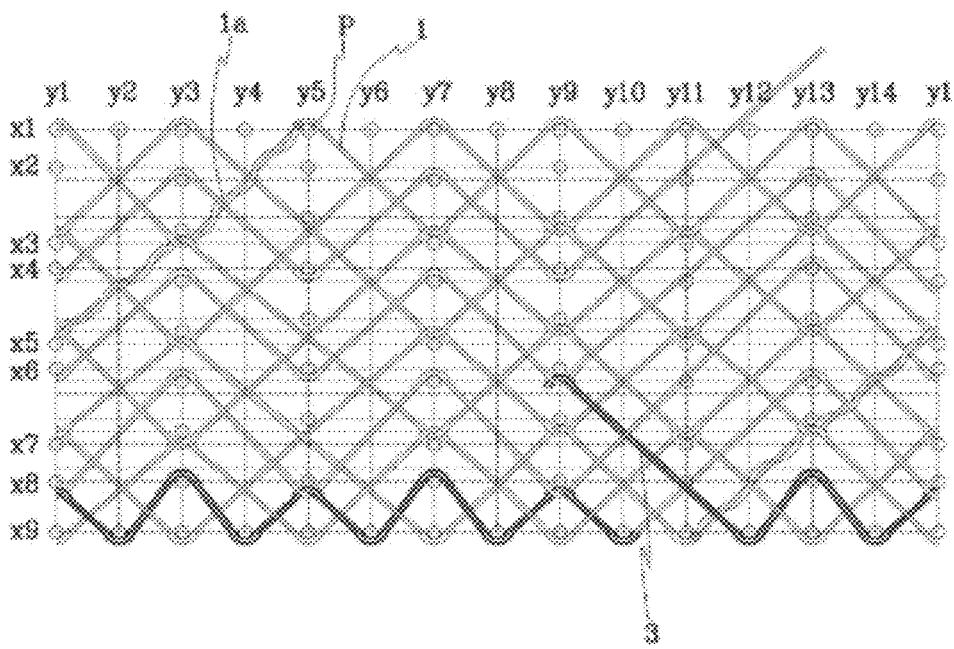

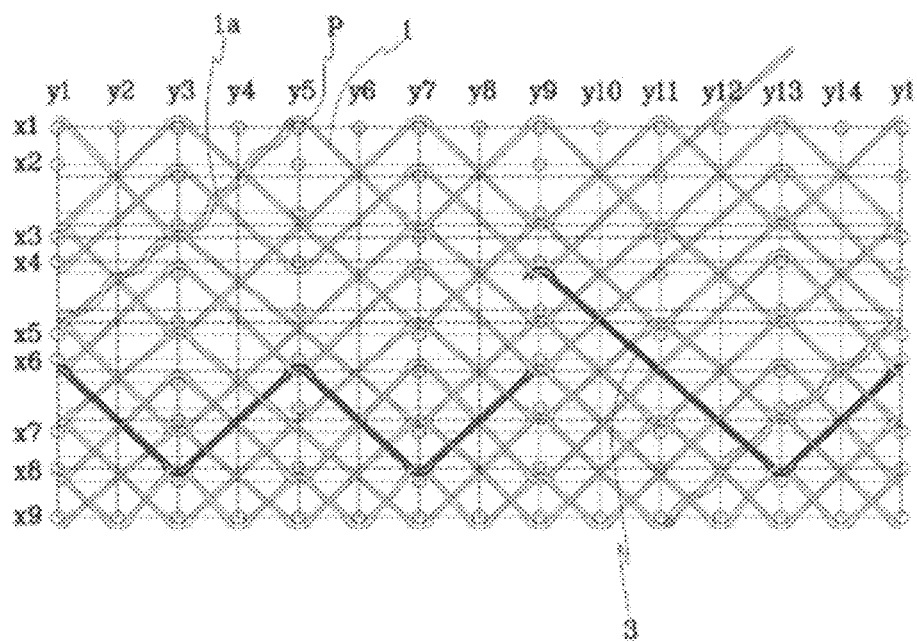
[Fig. 10]
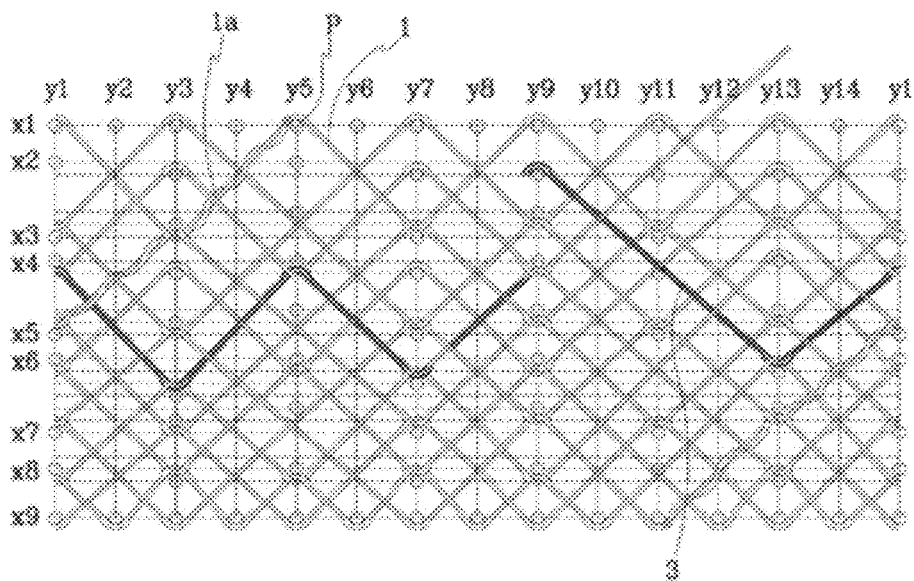
[Fig. 11]

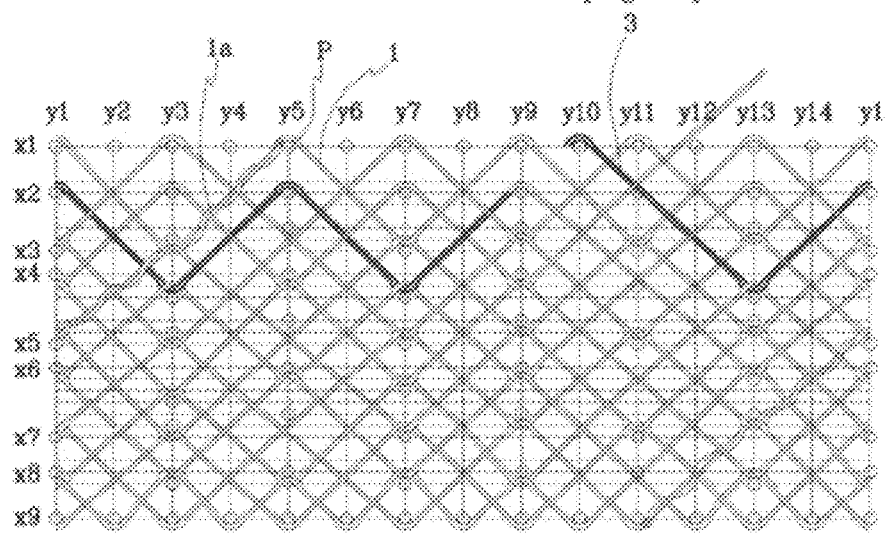
[Fig. 12]
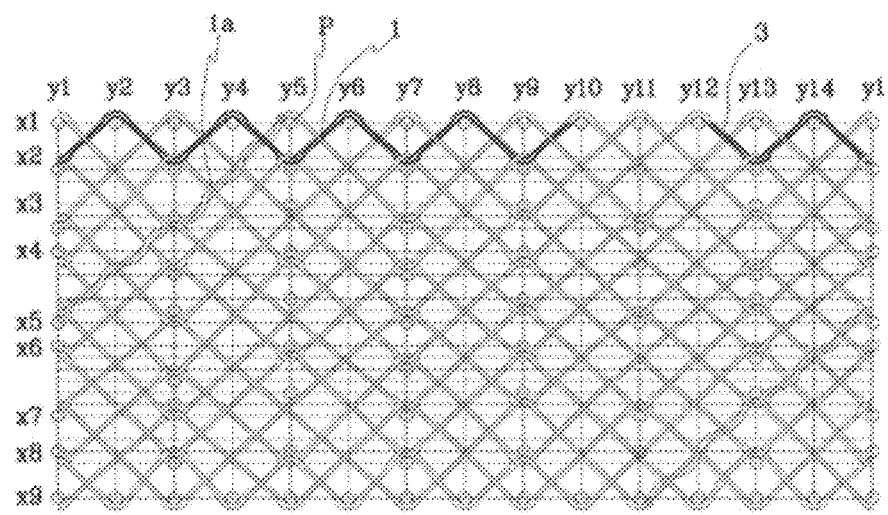
[Fig. 13]
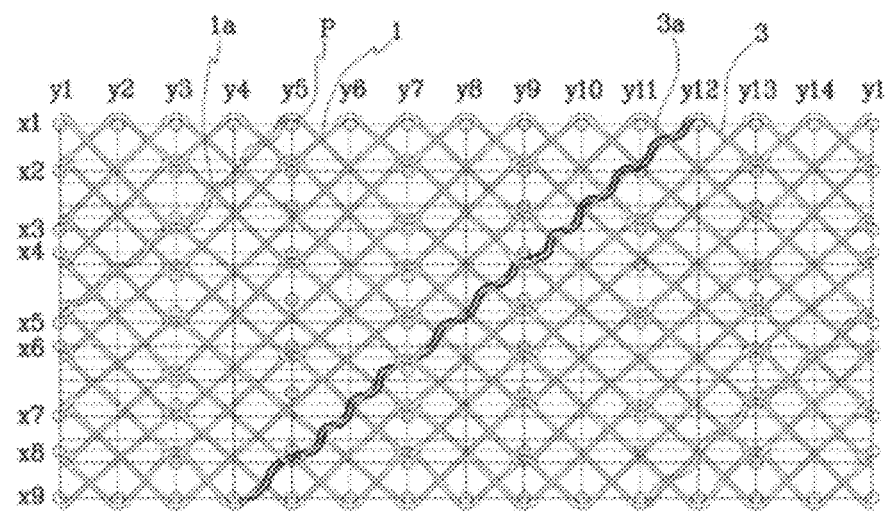
[Fig. 14]

STENT AND METHOD FOR MANUFACTURING THE SAME

CROSS REFERENCE TO RELATED APPLICATIONS

This application is a divisional application of U.S. patent application Ser. No. 11/914,490 for a "Stent and Method for Manufacturing the Same" filed Nov. 15, 2007, and published Jun. 10, 2008, as U.S. Patent Application Publication No. 2008/0167709 A1, now abandoned.

FIELD OF THE INVENTION

The present invention relates to a stent and a method for manufacturing the same, and more particularly, to the stent that is improved in a quality by preventing the damage of a material thereof during a manufacturing process and a method for manufacturing the stent.

BACKGROUND

Generally, a stent may be inserted into a lumen of a human body, or into a lesion of a blood vessel in order to maintain a passageway of the lumen, or the blood vessel. The stent may be formed of a shape memory alloy such as nitinol maintaining a uniform expansion force at a temperature of the lumen. The stent may be formed in a cylindrical shape woven by wires, and the cylindrical stent may be formed of two thin long members successively woven repeatedly in order to have a good expansion force (elastic force) in a radial direction. That is, a plurality of pins are disposed on a cylindrical manufacturing frame. Distances between the pins are same as each other. The two thin, long members each having a length of several meters are woven one after the other on the pins repeatedly. The thin, long members may be a wire member. At this point, during one member is woven, the other is in a standby status.

However, during one wire member is woven, the other wire member is left twisted or waved. Therefore, the wire members may be damaged during the above-described process, thereby being reduced in their elastic force and thus deteriorating the quality of the product.

SUMMARY

The present invention has been made in an effort to solve the above-described problems. It is an object of the present invention to provide a method of manufacturing a stent, which can prevent the wire members from being damaged during manufacturing processes of the stent, thereby improving the quality of the products.

Another object of the present invention is to provide a stent that can maintain the elastic force in a radial direction thereby easily inserted into or removed from the lesion and can prevent itself from inadvertently moving away from the lesion, thereby increasing a healing effect on a patient and a method for manufacturing the stent.

Still another object of the present invention is to provide a stent that is reduced in a diameter to a desired level when it is to be inserted in the lesion and thus can be easily inserted using an introducer, thereby reducing a pain of a patient and a method for manufacturing the stent.

In order to achieve the above-described objects, the present invention provides a method of manufacturing a stent, including: forming a first cylindrical mesh structure by bending a first member in a zigzag-shape having peaks and valleys and a plurality of turns wound around an outer circumference of a manufacturing frame; and forming a second cylindrical mesh structure by bending a second member in a zigzag-shape having peaks and valleys and a plurality of turns wound around an outer circumference of a manufacturing frame, wherein a bending track the second member crosses a bending track of the first member.

Preferably, the method may further include, after the first cylindrical mesh structure is formed, forming a first strut formed of a spirally twisted strut that is formed at a point where a distal end of the first member meets a proximal end of the first member.

Preferably, the method may further include, after the second cylindrical mesh structure is formed, forming a second strut formed of a spirally twisted strut that is formed at a point where a distal end of the second member meets a proximal end of the second member.

Preferably, the peaks and valleys of different turns of the first member are crossed and interlocked each other when the peaks and valleys of the different turns of the first member meet each other during the first cylindrical mesh structure is formed.

Preferably, the peaks and valleys of different turns of the second member are crossed and interlocked each other when the peaks and valleys of different turns of the second member meet each other during the second cylindrical mesh structure is formed.

According to another aspect of the present invention, there is provided a method of manufacturing a stent, including: providing a plurality of pins on a cylindrical surface of a cylindrical manufacturing frame and setting one of a plurality of pins as a starting point; winding a first member around the cylindrical manufacturing frame from the starting point to an end of the cylindrical manufacturing frame while being bent in a zigzag-shape to form peaks and valley with reference to the pins and having a plurality of turns; winding the first member around the cylindrical manufacturing frame from the end of the cylindrical manufacturing frame to the starting point while being bent in a zigzag-shape to form peaks and valley with reference to the pins and having a plurality of turns, the peaks and valley are crossed and interlocked each other when the peaks and valleys meet each other; forming a strut by spirally twisting a distal end portion of the first member and a proximal end portion of the first member after the peaks and valleys of the first member are formed; winding a second member around the cylindrical manufacturing frame from a starting point to an end of the cylindrical manufacturing frame while being bent in a zigzag-shape to form peaks and valley with reference to the pins and having a plurality of turns, wherein the starting point of the second member is disposed on a symmetrically opposite location of the starting point of the first member on the surface of the cylindrical manufacturing frame; winding the second member around the cylindrical manufacturing frame from the end of the cylindrical manufacturing frame to the starting point while being bent in a zigzag-shape to form peaks and valley with reference to the pins and having a plurality of turns, the peaks and valley are crossed and interlocked each other when the peaks and valleys meet each other; forming a strut by spirally twisting a distal end portion of the second member and a proximal end portion of the first member after the peaks and valleys of the first member are formed.

According to still another aspect of the present invention, there is provided a stent including: a first cylindrical mesh structure formed by bending a first member in a zigzag-shape having peaks and valleys and a plurality of turns wound around an outer circumference of a manufacturing frame; and a second cylindrical mesh structure formed by bending a second member in a zigzag-shape having peaks and valleys and a plurality of turns wound around an outer circumference of a manufacturing frame, wherein a bending track the second member crosses a bending track of the first member, wherein the first cylindrical mesh structure includes a first strut formed of a spirally twisted strut that is formed at a point where a distal end of the first member meets a proximal end of the first member; and the second cylindrical mesh structure includes a second strut formed of a spirally twisted strut that is formed at a point where a distal end of the second member meets a proximal end of the second member.

Preferably, the peaks and valleys of the first and second members are crossed and interlocked each other as a hook shape when they meet each other.

According to the present invention, a cylindrical stent with big mesh sizes is formed of the first member. After then the second member is crossed the track of the first member in order to form a cylindrical stent with small mesh sizes. Therefore, inadvertent displace of the first and second members from a target place can be prevented, and damages of materials forming of the first and second members are reduced thereby producing qualitative products.

In addition, according to the present invention, the distal end of the first member is continuously twisted around a part of the first member in order to form the first spirally twisted strut, and the distal end of the second member is continuously twisted around a part of the second member in order to form the second spirally twisted strut. Therefore, the spirally twisted struts increase an elastic force from a center to a radial direction. Also, when the stent is inserted to the lesion, the stent minimizes moving or overlapping to a longitudinal direction thereby the stent may be inserted easily. In addition, the increased elastic force of the stent to the radial direction maintains the stent fixed status at the lesion thereby maximizing the healing effect on a patient by preventing the stent moving from the lesion.

Also, according to the present invention, the first and second members have a crossed structure when the first and second members meet each other thereby minimizing a diameter of the stent. When the stent has the minimum diameter, the stent has the minimum volume. Therefore, the stent may be inserted easily using the introducer thereby reducing the pain of a patient.

BRIEF DESCRIPTION OF THE DRAWINGS

FIG. 1 is a perspective view illustrating a first embodiment of the present invention.

FIGS. 2 through 7 are developed views illustrating a working procedure of a first process.

FIGS. 8 through 14 are exploded views illustrating a working procedure of a second process.

DETAILED DESCRIPTION

The present invention will now be described more fully with reference to the accompanying drawings, in which an exemplary embodiment of the invention is shown.

FIG. 1 is a perspective view of a stent manufactured by a method of the present invention. FIGS. 2 through 14 are views illustrating consecutive processes of manufacturing the stent.

According to an embodiment of the present invention, a stent is formed of first and second members 1 and 3. FIGS. 2 through 7 are views illustrating a process, in which the cylindrical stent is formed of the first member on a manufacturing frame. FIGS. 8 through 14 are views illustrating a process, in which a fine mesh structure is formed of the second member.

The fine mesh structure is formed on the cylindrical stent formed of the first member. The first and second members 1 and 3 may be formed of a wire member, which may be coated in order to be inserted into a lumen or a lesion of a human body for a medical use. Hereinafter, the method of manufacturing the stent using a manufacturing frame J will be described in detail.

Referring to FIG. 1, the manufacturing frame J is cylindrical, and a plurality of pins P are disposed on a cylindrical surface on which the plurality of pins protrude in a radial direction. There are longitudinal gaps between the plurality of pins disposed on the cylindrical surface of the manufacturing frame J. Usually the gaps between the plurality of pins are same as each other, but the plurality of pins may be disposed with different gaps according to a design of the stent. It is preferable a plurality of holes are formed on the manufacturing frame J, and the plurality of pins are inserted into the plurality of holes. Referring to FIG. 2, according to the embodiment of the present invention, 9 rows of the plurality of pins (from top x1, x2, x3, ... x9; hereinafter pin and point are same location, and a usage of pin and point is mingled for convenience) are disposed in the longitudinal direction of the stent. At this point, 9 rows are arbitrary. 14 pins (from left y1, y2, y3, ... y13, y14, y1; since pin and point are same location, the usage of pin and point is mingled for convenience) are disposed on the first row x1 and the last row x9. Gaps between the 14 pins in the radial direction of the manufacturing frame J are identical to each other. 7 pins (y1, y3, y5, y7, y9, y11, y13) are disposed on the rows from x2 to x8. The number of pins disposed on the manufacturing frame j is not limited to this embodiment, and the stent may be manufactured using different numbers of pins.

Peaks and valleys are formed of the first member 1 successively from x1 to x9, in which the starting point is x1y5. The peaks and valleys of the first member are formed along the cylindrical surface of the manufacturing frame J, wherein a track of the first member 1 is bent zigzag. That is, referring to FIG. 2, the track of the first member 1 passes the points x3y3, x1y1, x3y13, x1y11, x3y9, x1y7, x5y3, x3y1, x5y13, x3y11, ... x9y9, and x7y7. Continuously, Peaks and valleys are formed of the first member 1 successively from x9 to x1 along the cylindrical surface of the manufacturing frame J, wherein a track of the first member 1 is bent zigzag. That is, the track of the first member 1 is continued to pass the points x7y7, x9y5, x7y3, x9y1, x7y13, x9y11, x7y9, x9y7, and x5y3. When the track of the first member 1 passes the points x7y3, x7y13, x7y9, and x5y3 at which the peaks and valley meet each other, the first member 1 may be crossed and interlocked simultaneously to the preceding first member in order to keep connected status. It is preferable peaks and valleys are crossed and interlocked simultaneously when peaks and valleys meet each other, and hereinafter this description may be omitted sometimes.

Continuously, referring to FIGS. 4, 5, and 6, the track of the peaks and valleys of the first member 1 is continuously formed on the cylindrical surface of the manufacturing frame. That is, referring FIG. 4, the track of the first member 1 passes continuously the points x5y3, x7y1, x5y13, x7y11, x5y9, x7y7, and x3y3 in order to form the stent. Also, referring FIG. 5, the track of the first member 1 passes continuously the points x3y3, x5y1, x3y13, x5y11, x3y9, x5y7, and x1y3 in order to form the stent. In addition, referring FIG. 6, the track of the first member 1 passes continuously the points x1y3, x3y1, x1y13, x3y11, x1y9, x3y7, and x1y5 (the starting point) in order to form the stent.

That is, the track of the first member 1 forms the peaks and valleys on the cylindrical surface of the manufacturing frame J starting from the starting point (x1y5). The track of the first member 1 passes from the first row to the last row. Then, the track of the first member 1 continuously passes from the last row to the first row, and the track of the first member 1 meets the preceding first member 1 at the starting point (x1y5). It is preferable, according to the present invention, peaks and valleys are crossed and interlocked simultaneously whenever peaks and valleys meet each other.

Referring to FIG. 7, a spirally twisted strut (Ia) is formed around the preceding first member at the starting point x1y5. The strut (Ia) increases an elastic force in radial and longitudinal directions, thereby reducing a longitudinal shrinkage when the stent is inserted. Therefore, the stent may be inserted easily, and the stent may keep a fixed status at the lesion with stability.

FIGS. 8 through 14 are views illustrating process for reducing a mesh size of the stent formed of the first member 1 using the second member 3. That is, it is preferable the second member 3 starts from the point x1y12. The point x Iy 12 is a symmetrically opposite location of the starting point x1y5 of the first member 1. Also, it is preferable the second member 3 crosses about half of the meshes formed by the first member 1, when the cylindrical stent is formed of the second member 3. This will now be described more fully with reference to FIGS. 8 through 14.

Peaks and valleys are formed of the second member 3 starting from the point x1y12 along the cylindrical surface of the manufacturing frame J, wherein a track of the second member 3 is bent zigzag from x1 to x9 successively. At this point, it is preferable the second member 3 crosses about a half of the each mesh formed of the first member 1 in order to form meshes of half size.

That is, referring to FIG. 8, the track of the second member 3 passes the points x1y12, x4y9, x2y7, x4y5, x2y3, x4y1, x2y13, x6y9, x4y7, x6y5, x4y3, . . . x6y13, and x9y1θ. Continuously, referring to FIG. 9, peaks and valleys are formed of the second member 3 along the cylindrical surface of the manufacturing frame J, wherein a track of the second member 3 is bent zigzag from x9 to x1 successively. That is, the track of the second member 3 is continued to pass the points x9y1θ, x8y9, x9y8, x8y7, x9y6, x8y5, x9y4, x8y3, x9y8, x8y1, x9y14, x8y13, x9y12, and x6y9. When the track of the second member 3 passes the points x8y9, x8y5, x8y1, and x6y9, wherein the peaks and valley meet each other at those points, the second member 3 may be crossed and interlocked simultaneously in order to keep connected status. It is preferable peaks and valleys are crossed and interlocked simultaneously whenever peaks and valleys meet each other.

Continuously, referring FIGS. 10, 11, and 12, the peaks and valleys of the second member 3 are formed on the cylindrical surface of the manufacturing frame. That is, referring FIG. 10, the track of the second member 3 passes continuously the points x6y9, x8y7, x6y5, x8y3, xβy1, x8y13, and x4y9 in order to form the stent. Also, referring to FIG. 11, the track of the second member 3 further passes continuously the points x4y9, x6y7, x4y5, x6y3, x4y1, xβy1, and x2y9 in order to form the stent. In addition, referring to FIG. 12, the track of the second member 3 further passes continuously the points x1y1O, x2y9, x1y8, x2y7, x1yβ, x2y5, x1y4, x2y3, x1y2, x2y1, x1y14, x2y13, and x1y12 (the starting point of the second member 3) in order to form the stent.

That is, the track of the second member 3 forms the peaks and valleys on the cylindrical surface of the manufacturing frame J starting from the starting point x1y12 (x Iy 12 is a symmetrically opposite point of the starting point of the first member on the cylindrical surface). At this point, the track of the second member 3 passes from the first row to the last row. After then the track of the second member 3 continuously passes from the last row to the first row, and the track of the second member 3 meets the preceding second member 3 at the starting point x Iy 12. It is preferable, according to the present invention, peaks and valleys are crossed and interlocked simultaneously when peaks and valleys meet each other.

Continuously, referring to FIG. 14, another spirally twisted strut (3a) is formed around the preceding second member at the starting point x1y12. The strut (3a) increases an elastic force in radial and longitudinal directions, thereby reducing the longitudinal shrinkage when the stent is inserted. Therefore, the stent may be inserted easily, and the stent may keep a fixed status at the lesion with stability. It is preferable the struts (Ia and 3a) are disposed as symmetric spirals.

According to the present invention, the processes for the second member are conducted after the processes for the first member 1 are completed. Accordingly, the first and second members 1 and 3 may not be interlocked each other simultaneously, and unprocessed part (the end part of the first and second members that may be wire members) of the first and second members 1 and 3 may not be damaged during the manufacturing processes. Therefore, a working efficiency is increased, and a quality of products may be improved. Specially, the manufacturing method of the present invention may form a finer mesh structure with an easy working process and thus the quality of the stent may be more improved.

Also, according to the present invention, the first and second members 1 and 3 are crossed and interlocked each other when they meet each other. Accordingly, when the stent is constricted, the stent has a smaller diameter than a stent formed by the prior art in which peaks and valleys are continuously interlocked each other without crossing points. Therefore, according to the present invention, the stent may be inserted using an introducer having a smaller diameter.

The stent may be used in a field of medical equipments. That is, the stent may be inserted into a lumen of a human body, or into a lesion of a blood vessel in order to maintain a passageway of the lumen, or the blood vessel.

The invention claimed is:

1. A method of manufacturing a stent, comprising:
   forming a first cylindrical mesh structure by bending a first member in a zigzag-shape having peaks and valleys and a plurality of turns wound around an outer circumference of a manufacturing frame; and
   forming a second cylindrical mesh structure by bending a second member in a zigzag-shape having peaks and valleys and a plurality of turns wound around an outer circumference of a manufacturing frame;
   wherein a bending track of the second member crosses about half way between each of the meshes formed by the bending track of the first member;
   wherein the peaks and valleys of different turns of the first member are crossed and interlocked with each other when the peaks and valleys of the different turns of the first member meet each other during the formation of the first cylindrical mesh structure; and
   wherein the peaks and valleys of different turns of the second member are crossed and interlocked with each other when the peaks and valleys of different turns of the second member meet each other during the formation of the second cylindrical mesh structure.

2. The method of claim 1, further comprising, after the first cylindrical mesh structure is formed, forming a first strut formed of a spirally twisted strut that is formed at a point where a distal end of the first member meets a proximal end of the first member.

3. The method of claim 1, further comprising, after the second cylindrical mesh structure is formed, forming a second strut formed of a spirally twisted strut that is formed at a point where a distal end of the second member meets a proximal end of the second member.

4. A stent manufactured according to the method of claim 1.

5. A method of manufacturing a stent, comprising:
providing a plurality of pins on a cylindrical surface of a cylindrical manufacturing frame and setting one of a plurality of pins as a starting point;
winding a first member around the cylindrical manufacturing frame from the starting point to an end of the cylindrical manufacturing frame while being bent in a zigzag-shape to form peaks and valleys with reference to the pins and having a plurality of turns;
winding the first member around the cylindrical manufacturing frame from the end of the cylindrical manufacturing frame to the starting point while being bent in a zigzag-shape to form peaks and valleys with reference to the pins and having a plurality of turns, the peaks and valley are crossed and interlocked each other when the peaks and valleys meet each other;
forming a strut by spirally twisting a distal end portion of the first member and a proximal end portion of the first member after the peaks and valleys of the first member are formed;
winding a second member around the cylindrical manufacturing frame from a starting point to an end of the cylindrical manufacturing frame while being bent in a zigzag-shape to form peaks and valleys with reference to the pins and having a plurality of turns, wherein the starting point of the second member is disposed on a symmetrically opposite location of the starting point of the first member on the surface of the cylindrical manufacturing frame;
winding the second member around the cylindrical manufacturing frame from the end of the cylindrical manufacturing frame to the starting point while being bent in a zigzag-shape to form peaks and valleys with reference to the pins and having a plurality of turns, wherein the peaks and valleys are crossed and interlocked each other when the peaks and valleys meet each other; and
forming a strut by spirally twisting a distal end portion of the second member and a proximal end portion of the first member after the peaks and valleys of the first member are formed;
wherein a bending track of the second member crosses about half way between each of the meshes formed by the bending track of the first member.

6. A stent manufactured according to the method of claim 5.

* * * * *